(12) United States Patent
Cortez, Jr. et al.

(10) Patent No.: US 10,695,524 B2
(45) Date of Patent: *Jun. 30, 2020

(54) NEBULIZER SYSTEMS, APPARATUS AND METHODS FOR RESPIRATORY THERAPY

(71) Applicant: Vapotherm, Inc., Exeter, NH (US)

(72) Inventors: Felino V. Cortez, Jr., Bowie, MD (US); William F. Niland, Arnold, MD (US)

(73) Assignee: VAPOTHERM, INC., Exeter, NH (US)

( * ) Notice: Subject to any disclaimer, the term of this patent is extended or adjusted under 35 U.S.C. 154(b) by 379 days.

This patent is subject to a terminal disclaimer.

(21) Appl. No.: 15/636,196

(22) Filed: Jun. 28, 2017

(65) Prior Publication Data

US 2017/0361055 A1 Dec. 21, 2017

Related U.S. Application Data

(63) Continuation of application No. 14/559,724, filed on Dec. 3, 2014, now Pat. No. 9,717,879, which is a
(Continued)

(51) Int. Cl.
*A61M 16/14* (2006.01)
*A61M 11/02* (2006.01)
(Continued)

(52) U.S. Cl.
CPC .......... *A61M 16/14* (2013.01); *A61M 11/002* (2014.02); *A61M 11/003* (2014.02);
(Continued)

(58) Field of Classification Search
CPC .. A61M 11/00; A61M 11/001; A61M 11/002; A61M 11/003; A61M 11/02;
(Continued)

(56) References Cited

U.S. PATENT DOCUMENTS 3,670,965 A 6/1972 Marand
3,864,326 A 2/1975 Babington
(Continued)

FOREIGN PATENT DOCUMENTS

RU 2009111135 A 10/2010
WO WO-2012160477 A1 11/2012

OTHER PUBLICATIONS

Extended European Search Report, Application No. EP 14 83 4470, dated Apr. 26, 2017, 8 pages.
(Continued)

*Primary Examiner* — Joseph D. Boecker
(74) *Attorney, Agent, or Firm* — White & Case LLP

(57) ABSTRACT

Nebulizer systems, apparatus, and methods are disclosed. The apparatus includes a body, a breathing gas inlet and outlet, and a barrier. The body is sized to be positioned within an adaptor of the nebulizer system. The breathing gas inlet and the breathing gas outlet are at opposite ends of the body. The barrier is coupled to the body. A plurality of holes are formed in the barrier. The plurality of holes open in a direction orthogonal to the breathing gas inlet. The system employs the apparatus in conjunction with a nebulizer and an adaptor. The method includes generating an aerosolized medicament, providing the aerosolized medicament to the adaptor, passing the aerosolized medicament through the barrier of the apparatus, providing a breathing gas to the apparatus, and flowing the aerosolized medicament and the breathing gas through the breathing gas outlet of the apparatus.

30 Claims, 5 Drawing Sheets

Related U.S. Application Data continuation of application No. 13/267,252, filed on Oct. 6, 2011, now Pat. No. 8,915,245.

(60) Provisional application No. 61/390,799, filed on Oct. 7, 2010.

(51) Int. Cl.
*A61M 16/08* (2006.01)
*A61M 11/00* (2006.01)
*A61M 16/10* (2006.01)
*A61M 16/16* (2006.01)

(52) U.S. Cl.
CPC ........ *A61M 11/02* (2013.01); *A61M 16/0816* (2013.01); *A61M 16/0833* (2014.02); *A61M 16/109* (2014.02); *A61M 11/005* (2013.01); *A61M 16/16* (2013.01); *A61M 2206/14* (2013.01)

(58) Field of Classification Search
CPC .......... A61M 16/0816; A61M 16/0833; A61M 16/109; A61M 16/14; A61M 16/142; A61M 16/16; A61M 2206/14; B05B 3/08
USPC ......................... 128/200.14, 200.18, 200.23, 128/203.16–203.18, 203.26; 239/275, 239/370, 461, 498, 504, 505, 518, 521, 239/523
See application file for complete search history.

(56) References Cited

U.S. PATENT DOCUMENTS

| | | |
|---|---|---|
| 3,949,743 A | 4/1976 | Shanbrom |
| 4,007,737 A | 2/1977 | Paluch |
| 4,094,317 A | 6/1978 | Wasnich |
| 4,171,962 A | 10/1979 | Kippel et al. |
| 4,177,945 A | 12/1979 | Schwartz et al. |
| 4,333,451 A | 6/1982 | Paluch |
| 4,520,812 A | 6/1985 | Freitag et al. |
| 4,558,708 A | 12/1985 | Labuda et al. |
| 4,620,670 A | 11/1986 | Hughes |
| 4,819,625 A | 4/1989 | Howe |
| 4,832,012 A | 5/1989 | Raabe et al. |
| 4,911,157 A | 3/1990 | Miller |
| 4,951,661 A | 8/1990 | Sladek |
| 5,226,411 A | 7/1993 | Levine |
| 5,461,695 A | 10/1995 | Knoch |
| 5,630,409 A | 5/1997 | Bono et al. |
| 5,813,401 A * | 9/1998 | Radcliff ............... A61M 16/208 128/200.14 |
| 6,166,025 A | 12/2000 | Harding et al. |
| 6,718,969 B1 * | 4/2004 | Rubin ............... A61M 15/0086 128/200.14 |
| 8,915,245 B2 * | 12/2014 | Cortez, Jr. ........ A61M 16/0833 128/200.18 |
| 9,717,879 B2 * | 8/2017 | Cortez, Jr. ............. A61M 16/14 |
| 2003/0150445 A1 | 8/2003 | Power et al. |
| 2004/0069307 A1 | 4/2004 | Rich et al. |
| 2004/0237178 A1 | 12/2004 | Landeros |
| 2005/0061318 A1 * | 3/2005 | Faram ............... A61M 16/0096 128/204.18 |
| 2006/0219243 A1 | 10/2006 | Walstrom |
| 2007/0128912 A1 | 6/2007 | Glaze et al. |
| 2008/0000470 A1 | 1/2008 | Minocchieri et al. |
| 2009/0062855 A1 | 3/2009 | Lemery et al. |
| 2010/0071693 A1 | 3/2010 | Allum et al. |
| 2010/0089395 A1 | 4/2010 | Power et al. |
| 2010/0154797 A1 | 6/2010 | Landis et al. |
| 2010/0258114 A1 | 10/2010 | Cortez, Jr. et al. |
| 2011/0108022 A1 * | 5/2011 | King ..................... A61M 11/06 128/200.14 |
| 2012/0272954 A1 | 11/2012 | Landis et al. |
| 2013/0081616 A1 | 4/2013 | Tatkov |
| 2013/0133645 A1 | 5/2013 | Lee et al. |
| 2018/0200469 A1 * | 7/2018 | Higginbotham ...... A61M 16/16 |

OTHER PUBLICATIONS

International Search Report and Written Opinion for PCT/US2014050382 dated Nov. 28, 2014.

International Search Report dated Apr. 21, 2013, Application No. PCT/US2013/022692 dated Aug. 7, 2014.

\* cited by examiner

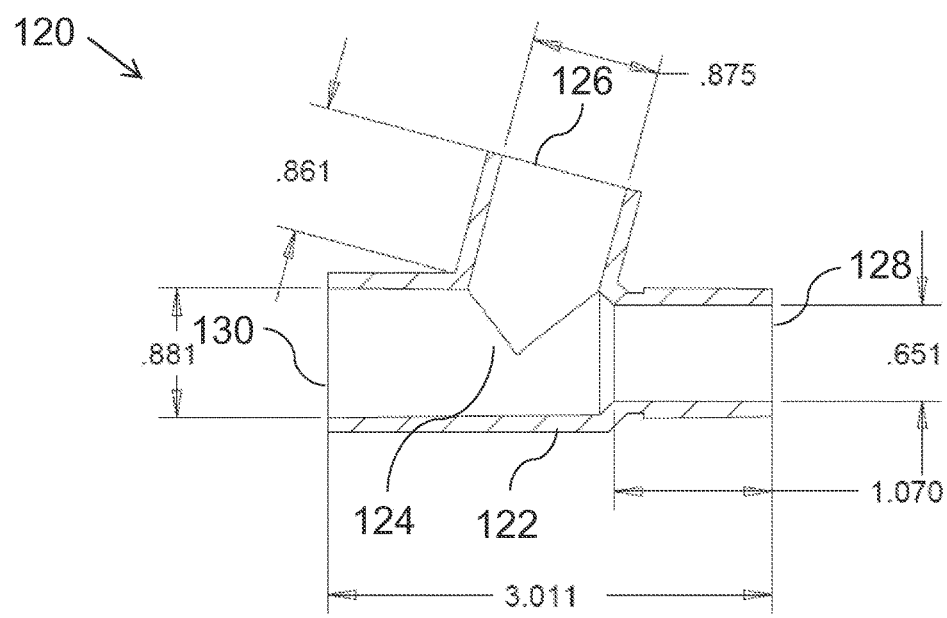
FIG. 4
PRIOR ART
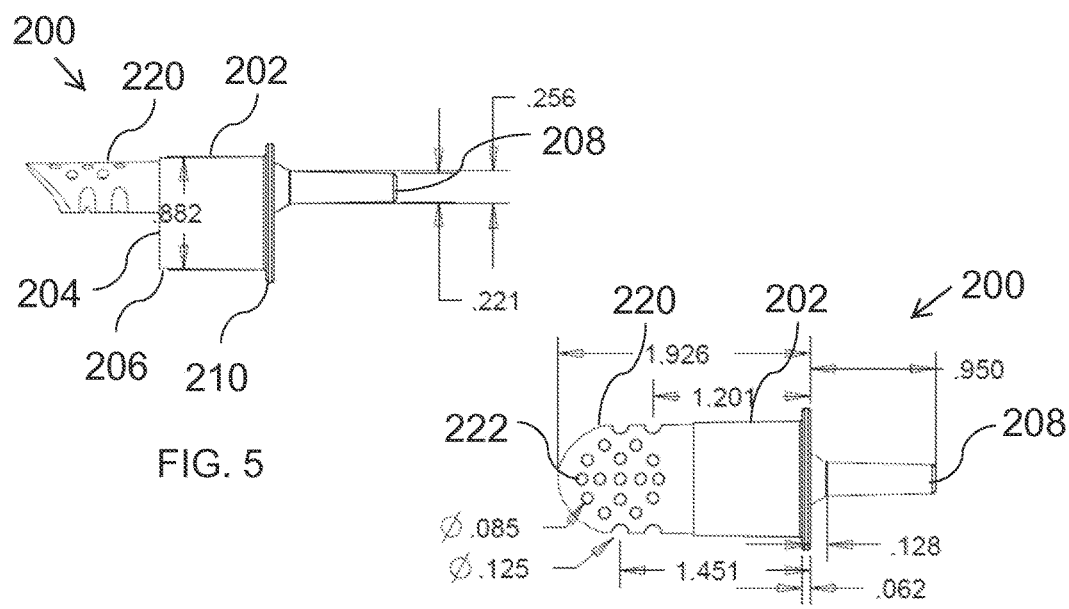
FIG. 5
FIG. 6

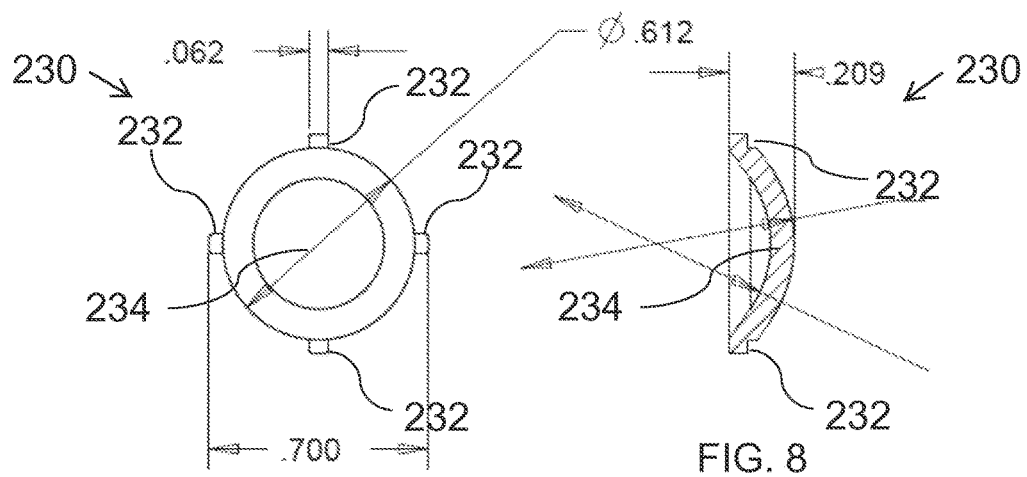
FIG. 7
FIG. 8
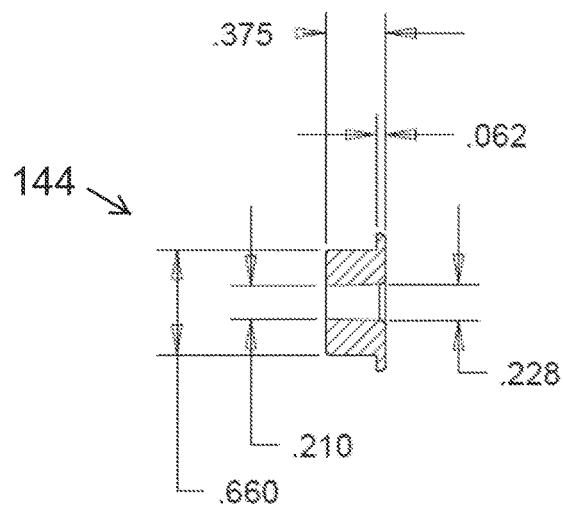
FIG. 9
PRIOR ART

300

```
┌─────────────────────────────────┐
│    Generate an aerosolized      │─── 310
│    medicament with a nebulizer  │
└─────────────────────────────────┘
                 │
                 ▼
┌─────────────────────────────────┐
│  Provide the aerosolized        │─── 320
│  medicament to an adaptor body  │
└─────────────────────────────────┘
                 │
                 ▼
┌─────────────────────────────────┐
│ Pass the aerosolized medicament │
│ in the adaptor body through a   │─── 330
│ plurality of holes in a barrier │
│ of an apparatus                 │
└─────────────────────────────────┘
                 │
                 ▼
┌─────────────────────────────────┐
│   Provide a breathing gas to a  │─── 340
│ breathing gas inlet of the      │
│ apparatus                       │
└─────────────────────────────────┘
                 │
                 ▼
┌─────────────────────────────────┐
│ Flow the aerosolized medicament │
│ and the breathing gas to the    │─── 350
│ breathing gas outlet of the     │
│ apparatus                       │
└─────────────────────────────────┘
```

FIG. 10

NEBULIZER SYSTEMS, APPARATUS AND METHODS FOR RESPIRATORY THERAPY

CROSS-REFERENCE TO RELATED APPLICATIONS

This application is a continuation of U.S. patent application Ser. No. 14/559,724 (currently allowed), filed Dec. 3, 2014, which is a continuation of U.S. patent application Ser. No. 13/267,252, (now issued as U.S. Pat. No. 8,915,245), filed Oct. 6, 2011, which claims priority to U.S. patent application No. 61,390,799, filed Oct. 7, 2010, entitled "NEBULIZER SYSTEMS, APPARATUS, AND METHODS FOR RESPIRATORY THERAPY," the contents of which are incorporated herein by reference in their entirety.

FIELD OF THE INVENTION

The present invention relates generally to respiratory therapy, and more particularly to nebulizer systems and apparatus for use in providing respiratory therapy.

BACKGROUND OF THE INVENTION

Patients with respiratory ailments may be administered supplemental breathing gases, such as oxygen, for example, to aid in respiration. These breathing gases are typically provided from a breathing gas supply, such as an oxygen tank. A delivery device, such as a nasal cannula, may be coupled to the breathing gas supply and inserted into a patient's nasal passages for delivery of the breathing gas to the patient for inhalation.

Separately, respiratory medications may be administered through inhalation directly to the patient's lungs. These respiratory medications may be aerosolized by a nebulizer in order to generate small particles of the medication, which facilitate distribution throughout the patient's lungs during inhalation. Conventional nebulizers draw liquid medicament from a liquid reservoir to form a nebulized aerosol for inhalation.

SUMMARY OF THE INVENTION

Aspects of the present invention are directed to nebulizer systems, apparatus, and methods for respiratory therapy.

In accordance with one aspect of the present invention, an apparatus for use with a nebulizer system is disclosed. The apparatus comprises a body, a breathing gas inlet, a breathing gas outlet, and a barrier. The body is sized to be positioned within an adaptor of the nebulizer system. The breathing gas inlet is at a first end of the body. The breathing gas outlet is at a second end of the body opposite the first end. The barrier is coupled to the body. A plurality of holes are formed in the barrier. The plurality of holes open in a direction orthogonal to the breathing gas inlet.

In accordance with another aspect of the present invention, a nebulizer system using the above apparatus is disclosed. The nebulizer system comprises a nebulizer, an adaptor, and the above apparatus. The nebulizer has a nebulizer outlet port. The nebulizer is operable to generate an aerosolized medicament and pass the aerosolized medicament through the nebulizer outlet port. The adaptor has an adaptor body, a nebulizer coupling port, an inlet port, and an outlet port. The nebulizer coupling port of the adaptor is coupled to the nebulizer outlet port of the nebulizer. The apparatus is positioned within the adaptor body.

In accordance with still another aspect of the present invention, a method of providing respiratory therapy using the above system is disclosed. The method comprises generating an aerosolized medicament with the nebulizer, providing the aerosolized medicament through the nebulizer coupling port of the adaptor to the adaptor body, passing the aerosolized medicament in the adaptor body through the plurality of holes in the barrier of the apparatus to the body of the apparatus, providing a breathing gas through the inlet port of the adaptor to the breathing gas inlet of the apparatus, and flowing the aerosolized medicament and the breathing gas through the body of the apparatus to the breathing gas outlet of the apparatus.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIG. 1 is an exploded view of an exemplary nebulizer system in accordance with aspects of the present invention;

FIG. 2 is a cross-sectional view of the assembled nebulizer system of FIG. 1;

FIG. 3 is another cross-sectional view of the assembled nebulizer system of FIG. 1 include a breathing gas source and a breathing device;

FIG. 4 is a cross-sectional view of a prior art adaptor for use in the nebulizer system of FIG. 1;

FIG. 5 is a side view of an insert apparatus of the nebulizer system of FIG. 1 in accordance with aspects of the present invention;

FIG. 6 is a top view of the insert apparatus of FIG. 5;

FIG. 7 is a front view of a baffle of the insert apparatus of FIG. 5 in accordance with aspects of the present invention;

FIG. 8 is a side view of the baffle of FIG. 7;

FIG. 9 is a side view of a prior art connector of the nebulizer system of FIG. 1; and FIG. 10 is a flowchart illustrating an exemplary method for providing respiratory therapy in accordance with aspects of the present invention.

DETAILED DESCRIPTION OF THE INVENTION

Certain terminology is used herein for convenience only and is not to be taken as a limitation on the present invention. The terminology includes the words specifically mentioned, derivatives thereof and words of similar import. The following describes exemplary embodiments of the invention. It should be understood based on this disclosure, however, that the invention is not limited by the exemplary embodiments of the invention.

Embodiments of the present invention are directed to systems, apparatus, and methods for providing respiratory therapy to a patient. These exemplary embodiments may be particularly suitable for providing an aerosolized medicament to a patient via a breathing device, such as a nasal cannula. Suitable medicaments for use with the disclosed nebulizer systems will be known to one of ordinary skill in the art. Additionally, while the exemplary embodiments are described herein for use in conjunction with a nasal cannula, it will be understood that other breathing devices may be used without departing from the scope of the invention.

Referring now to the drawings, FIGS. 1-9 are diagrams illustrating an exemplary nebulizer system 100 in accordance with aspects of the present invention. Nebulizer system 100 may be used to provide respiratory therapy to a patient. Generally, nebulizer system 100 includes a nebulizer 110, an adaptor 120, and an insert apparatus 200. Additional details of nebulizer system 100 will be described herein.

Figure 1:
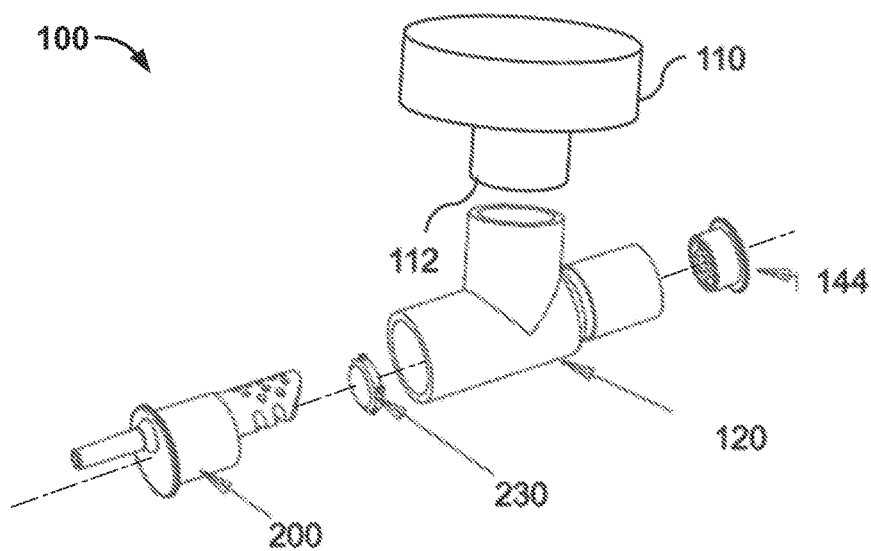
Figure 3:
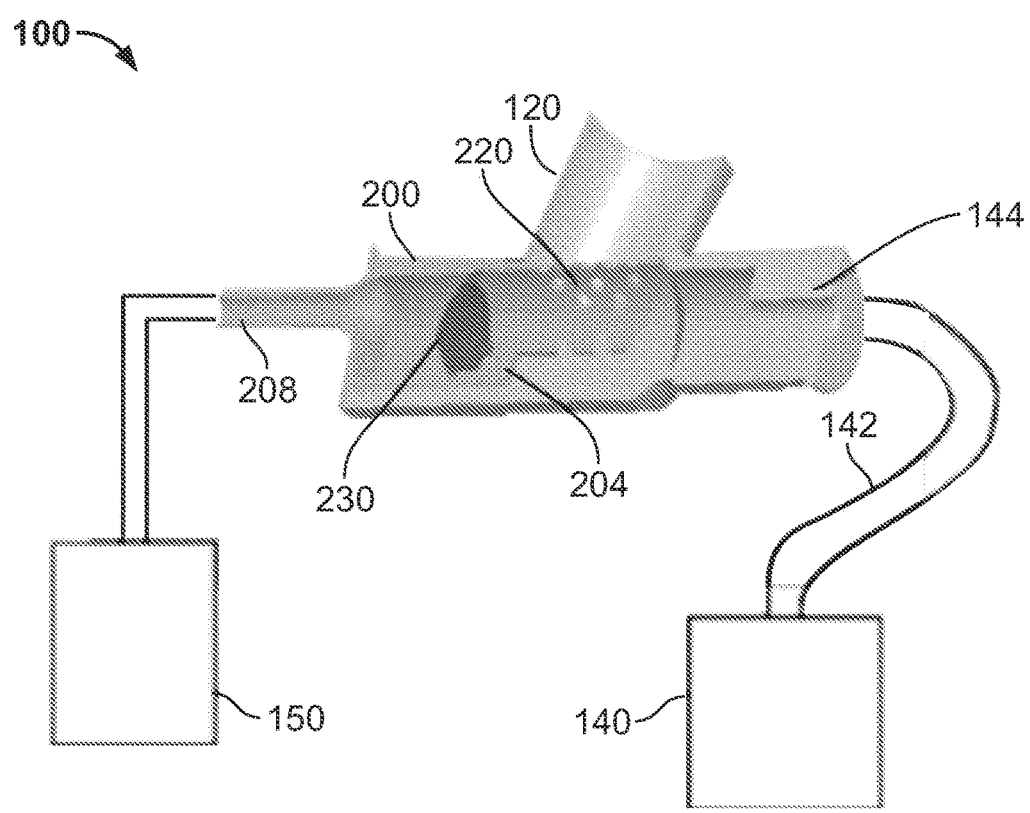

Nebulizer 110 is operable to generate an aerosolized medicament. Nebulizer 110 includes an aerosol generator (not shown) that aerosolizes a medicament contained within nebulizer 110. Nebulizer 110 also includes an outlet port 112 at the bottom of nebulizer 110, as shown in FIGS. 1 and 3. For example, nebulizer 110 may use an electrical signal to draw fluid into a vibratory aerosolization element (not shown), to produce an aerosol mist in the form of a low velocity cloud of aerosolized medicament. The cloud of aerosolized medicament exits nebulizer 110 by passing through outlet port 112. In an exemplary embodiment, nebulizer 110 is the Aeroneb® Professional nebulizer, available from Aerogen, Ltd of Galway, Ireland. However, essentially any conventional nebulizer may be used, as would be understood by one of ordinary skill in the art from the description herein.

Adaptor 120 is couplable to nebulizer 110. A suitable prior art adaptor 120 is shown in FIG. 4. Adaptor 120 has an adaptor body 122 defining an internal mixing chamber 124. Adaptor body 122 may be approximately T-shaped. Adaptor 120 includes a nebulizer coupling port 126, an inlet port 128, and an outlet port 130. Ports 126, 128, 130 each opening into internal mixing chamber 124. In use, the nebulizer coupling port 126 of adaptor 120 is coupled to the outlet port of nebulizer 110 in order to receive the cloud of aerosolized medicament. The cloud of aerosolized medicament may then pass into the internal mixing chamber 124. In an exemplary embodiment, adaptor 120 is the Aerogen T-Adaptor, available from Aerogen, Ltd of Galway, Ireland. Other suitable adaptors for use with the present invention will be known to one of ordinary skill in the art from the description herein.

Insert apparatus 200 is positionable within adaptor 120, FIGS. 5 and 6 are diagrams of an exemplary insert apparatus 200 for use with a nebulizer system in accordance with aspects of the present invention. Insert apparatus 200 has an apparatus body 202 sized to be positioned within adaptor 120. In an exemplary embodiment, body 202 has a cylindrical shape, as shown in FIGS. 5 and 6. Insert apparatus 200 has a breathing gas inlet 204 formed at one end 206 of body 202, and a breathing gas outlet 208 formed at an opposite end 210 of body 202. As shown in FIG. 5, it may be desirable that breathing gas inlet 204 have a greater circular cross-sectional area than breathing gas outlet 208. The use of a breathing gas inlet 204 having a greater cross-sectional area allows a tight fit connection between insert apparatus 200 and adaptor 120, and provides a seat for baffle 230 at a step change between breathing gas inlet 204 and breathing gas outlet 208.

Insert apparatus 200 further includes a barrier 220. Barrier 220 is coupled to body 202 of insert apparatus 200. A plurality of holes 222 are formed in barrier 220. The plurality of holes 222 may open in a direction orthogonal to the opening of breathing gas inlet 204. In an exemplary embodiment, barrier 220 extends outward from end 206 beyond breathing gas inlet 204, as shown in FIG. 5. In an alternative embodiment, barrier 220 may comprise a wall of body 202 formed between ends 206 and 210 (not shown). The plurality of holes 222 in barrier 220 are desirably sized to permit the passage of aerosolized medicament through holes 222 while inhibiting the passage of liquid droplets of medicament. Aerosol generated by nebulizers come in different particle size distribution. Barrier 220 acts like a sieve by allowing the smaller, desirable particles of medicament (sized for respiratory tract penetration and deposition) to pass through barrier 220 and be picked up by the flow of breathing gas. The larger-sized particles of medicament (too large to be respirable) are stopped by barrier 220. Instead, the larger particles coalesce and form liquid droplets, and adhere to the inside surface of adaptor 120. These droplets collect and remain in the bottom surface of adaptor 120. In an exemplary embodiment, holes 222 may have a diameter of approximately 62-93 µm.

Figure 2:
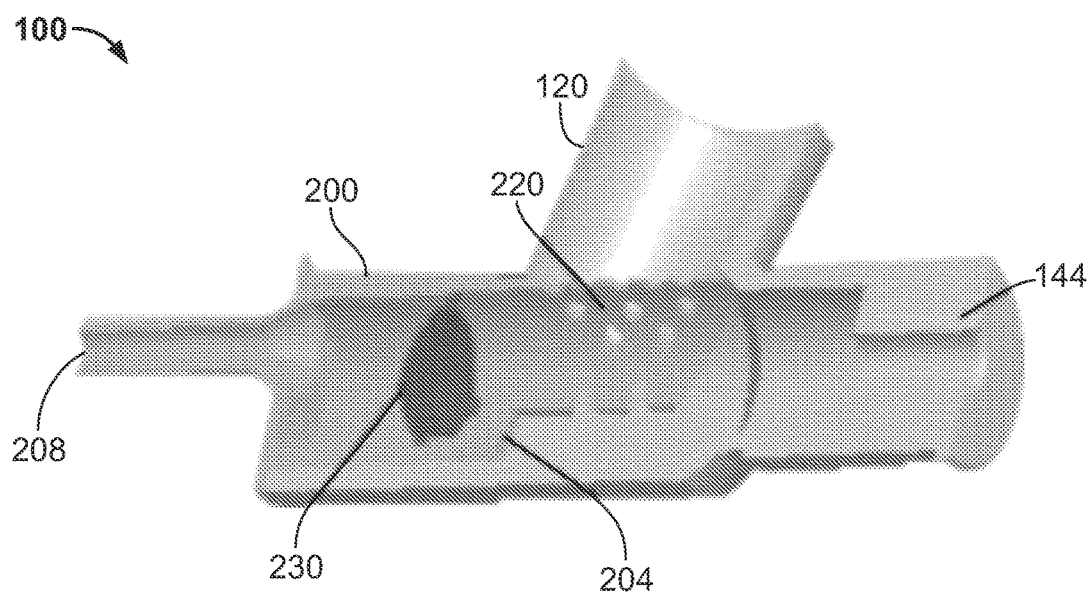

Insert apparatus 200 may further include a baffle 230. Baffle 230 is positioned within body 202 of insert apparatus 200. Baffle 230 may be physically separate from insert apparatus 200 (as shown in FIG. 1), or may be integrally formed within body 202 of insert apparatus 200. Baffle 230 is desirably positioned approximately at a circular cross-sectional center of body 202, downstream of both breathing gas inlet 204 and holes 222, as shown in FIGS. 2 and 3. Baffle 230 may include prongs 232 for fixing baffle in place within body 202. Baffle 230 may be fixed in place by fixing prongs 232 to an inner portion of body 202, for example, with adhesive. In an exemplary embodiment, baffle 230 has a circular shape, as shown in FIG. 7. Baffle 230 is formed so that its diameter is less than the diameter of the inner wall of body 202. Thus, when baffle is positioned approximately at the cross-sectional center of body 202, a channel is defined between the outer peripheral edge of baffle 230 and the inner wall of body 202.

Baffle 230 desirably includes a concavity 234, as shown in FIG. 8. Baffle 230 may be positioned within body 202 so that the concavity 234 faces toward breathing gas inlet 204. This may be desirable because as the breathing gas flow enters adaptor 120 through connector 144, it picks up the small particles of aerosolized medicament. Due to the high rate of flow entering adaptor 120, liquid droplets may also be drawn into the gas flow. Baffle 230 stops and/or deflects the liquid droplets back into adaptor 120, allowing a mixture of droplet-free aerosolized medicament and high flow breathing gas to exit through breathing gas outlet 208 to the breathing device 150. Allowing liquid droplets to enter breathing device 150 may generate extra resistance to airflow and create additional build up of condensation along the inner walls of the breathing device, which minimizes the delivery of effective-sized particles.

Suitable materials for forming insert apparatus 200 include, for example, K-Resin, polycarbonate, and/or silicone. Insert apparatus 200 (including baffle 230) may be formed from the same materials as adaptor 120. Other materials for use in forming insert apparatus 200 will be known to one of ordinary skill in the art from the description herein.

As set forth above, insert apparatus 200 is positionable inside the adaptor body 122 of adaptor 120. Apparatus 200 may be inserted into adaptor 120 through outlet port 130. When inserted, it is desirable that the plurality of holes 222 formed in barrier 220 open toward nebulizer coupling port 126 of adaptor 120. In an exemplary embodiment, this may be achieved by fixing insert apparatus 200 to adaptor body 122 with adhesive. Alternatively, the orientation of insert apparatus 200 in adaptor 120 may be fixed via a slotted or tongue and groove connection (not shown). Other means for fixing the orientation of insert apparatus 200 within adaptor 120 will be known to one of ordinary skill in the art from the description herein. When insert apparatus 200 is positioned within adaptor 120, the breathing gas outlet 208 and end 210 may extend through outlet port 130 of adaptor 120, and outside of adaptor body 122. This may facilitate connection with a breathing device, as described below.

Nebulizer system 100 may further comprise a source of breathing gas 140. Source 140 generates breathing gas for inhalation by a user of nebulizer system 100. Source 140 may desirably generate heated and humidified breathing gas. In an exemplary embodiment, breathing gas source 140 is the Vapotherm 2000i, the Vapotherm Precision Flow, the Vapotherm Flowrest System, or the Vapotherm Careflow system provided by Vapotherm, Inc of Stevensville, Md., USA. Other suitable breathing gas sources will be known to one of ordinary skill in the art from the description herein.

Source 140 is coupled to provide breathing gas to adaptor 120 via delivery tube 142. Delivery tube 142 couples breathing gas source 140 to the inlet port 128 of adaptor 120. Nebulizer system 100 may also include a connector 144 for coupling delivery tube 142 with adaptor 120, as shown in FIG. 9. Connector 144 connects delivery tube 142 with the inlet port 128 of adaptor 120 to ensure the flow of breathing gas from source 140 enters the internal mixing chamber 124 of adaptor 120, as shown in FIG. 3. The delivery tube 142 and connector 144 used with the present invention may be selected based on the adaptor 120 that is used. Suitable delivery tubes and connectors will be known to one of ordinary skill in the art from the description herein.

Nebulizer system 100 may further include a breathing device 150. Breathing device 150 is coupled to provide the breathing gas and aerosolized medicament from adaptor 120 to a user. Breathing device 150 may be coupled to outlet port 130 of adaptor 120. Alternatively, where breathing gas outlet 208 and end 210 extend through outlet port 130, breathing device 150 may be coupled to breathing gas outlet 208, as shown in FIG. 3. In an exemplary embodiment, breathing device 150 is a nasal cannula. Other suitable breathing devices will be known to one of ordinary skill in the art from the description herein.

FIG. 10 is a flowchart illustrating an exemplary method 300 for providing respiratory therapy in accordance with aspects of the present invention. Method 300 may be implemented using the exemplary nebulizer system 100 described above. Generally, method 300 includes generating an aerosolized medicament, providing the aerosolized medicament to an adaptor body, passing the aerosolized medicament through holes in a barrier, providing a breathing gas to the adaptor body, and flowing the aerosolized medicament and the breathing gas from the adaptor. Additional details of method 300 will be described herein with reference to nebulizer system 100.

In step 310, an aerosolized medicament is generated. In an exemplary embodiment, nebulizer 110 generates an aerosolized medicament, substantially as described above.

In step 320, the aerosolized medicament is provided to an adaptor body. In an exemplary embodiment, the aerosolized medicament generated by nebulizer 110 pass out of the nebulizer through the nebulizer output port 112. Adaptor 120 is coupled to nebulizer 110 such that the aerosolized medicament passes in through nebulizer coupling port 126 to the internal mixing chamber 124 of adaptor 120.

In step 330, the aerosolized medicament is passed through holes in a barrier. In an exemplary embodiment, the aerosolized medicament passes into adaptor 120 via nebulizer coupling port 126, and is drawn through the plurality of holes 222 in barrier 220 of insert apparatus 200. The aerosolized medicament may pass through holes 222 and into body 202 of the apparatus 200 via breathing gas inlet 204, as shown in FIG. 3. Alternatively, where barrier 220 comprises a wall of insert apparatus 200, the aerosolized medicament may pass through holes 222 directly into body 202 of apparatus 200. It is desirable that the aerosolized medicament pass through holes 222 in order to prevent liquid droplets of medicament from being delivered to a user. Accordingly, the shape of barrier 220 and the size of holes 222 are desirably selected such that barrier inhibits droplets of medicament from entering body 202 of apparatus 200.

In step 340, breathing gas is provided to the adaptor body. In an exemplary embodiment, breathing gas from source 140 to adaptor 120. Breathing gas may be provided via delivery tube 142 to the inlet port 128 of adaptor 120. The breathing gas provided to adaptor 120 flows through breathing gas inlet 204 of apparatus 200, and into body 202 of apparatus 200, as shown with arrows in FIG. 3.

In step 350, the aerosolized medicament and breathing gas are flowed through an apparatus body to a breathing gas outlet. In an exemplary embodiment, the aerosolized medicament and breathing gas are mixed with each other in the body 202 of apparatus 200. The mixture then flows through body 202 of apparatus 200 and out of the breathing gas outlet 208. When apparatus 200 includes baffle 230, the mixture of aerosolized medicament and breathing gas may flow around baffle 230, in the channel between the outer edge of baffle 230 and the inner wall of body 202. The mixture of aerosolized medicament and breathing gas may then be delivered to a patient with breathing device 150.

The exemplary embodiments of the present invention described above may provide certain advantages over conventional systems, apparatus, and methods for respiratory therapy. In particular, the insert apparatus described above provides numerous advantages over conventional adaptors which lack such an insert. The insert enables particles of aerosolized medicament to blend with the flow of breathing gas while filtering out and trapping condensed droplets of medicament inside the adaptor body. This significantly minimizes liquid droplets from getting into the gas stream and exiting into the breathing device, where they may interfere with or degrade respiratory treatment.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. Apparatus for use with a nebulizer system, the apparatus comprising:
   an adaptor having a nebulizer coupling port, an inlet port, an outlet port, and a mixing chamber between the inlet port and the outlet port, wherein the inlet port adjoins the mixing chamber;
   an insert having:
      a body sized to be positioned within the adaptor;
      a breathing gas inlet at a first end of the body;
      a breathing gas outlet at a second end of the body opposite the first end; and a barrier coupled to the body and disposed between the nebulizer coupling port and the mixing chamber, wherein a plurality of holes are formed in the barrier, and wherein each of the plurality of holes is substantially circular.

2. The apparatus according to claim 1, wherein at least three of the plurality of holes are collinear.

3. The apparatus according to claim 1, wherein the plurality of holes comprises at least four holes.

4. The apparatus according to claim 1, wherein the plurality of holes are positioned on a curved portion of the barrier.

5. The apparatus according to claim 1, wherein the plurality of holes open towards the nebulizer coupling port of the adaptor.

6. The apparatus according to claim 1, wherein the barrier is shaped to inhibit passage of liquid droplets from the nebulizer coupling port to the outlet port.

7. The apparatus according to claim 1, wherein the barrier is shaped to conform to an inner surface of the adaptor.

8. The apparatus according to claim 1, wherein the barrier is shaped to guide liquid droplets to an inside surface of the mixing chamber.

9. The apparatus according to claim 1, wherein the holes are sized to inhibit passage of liquid droplets from the nebulizer coupling port to the outlet port.

10. The apparatus according to claim 1, wherein each of the plurality of holes has a diameter of approximately 62-93 µm.

11. A nebulizer system comprising:
a nebulizer having a nebulizer outlet port, the nebulizer operable to generate an aerosolized medicament and pass the aerosolized medicament through the nebulizer outlet port;
an adaptor having an adaptor body, a nebulizer coupling port, an inlet port, and an outlet port, the nebulizer coupling port of the adaptor coupled to the nebulizer outlet port of the nebulizer; and
an insert positioned within the adaptor and comprising a barrier such that the barrier is disposed between the nebulizer coupling port and a mixing chamber wherein a plurality of holes are formed in the barrier, wherein each of the plurality of holes is substantially circular, wherein at least three of the plurality of holes are collinear, and wherein the insert includes a breathing gas outlet.

12. The nebulizer system according to claim 11, wherein the plurality of holes permits passage of aerosol from the nebulizer coupling port to the outlet port.

13. The nebulizer system according to claim 11, wherein the holes are sized to inhibit passage of liquid droplets from the nebulizer coupling port to the outlet port of the adaptor.

14. The nebulizer system according to claim 11, wherein the plurality of holes comprises at least four holes.

15. The nebulizer system according to claim 11, wherein each of the plurality of holes has a diameter of approximately 62-93 µm.

16. The nebulizer system according to claim 11, further comprising:
a source of breathing gas; and
a delivery tube coupling the source of breathing gas with the inlet port of the adaptor.

17. The nebulizer system according to claim 16, further comprising a connector, the connector connecting the delivery tube with the inlet port of the adaptor.

18. A method of providing respiratory therapy, the method comprising:

directing aerosolized medicament, generated by a nebulizer, into an adaptor body that is coupled to the nebulizer through an inlet port, wherein the inlet port adjoins a mixing chamber;
directing the aerosolized medicament within the adaptor body into the mixing chamber through an insert comprising a barrier with a plurality of holes formed in the barrier,
wherein each of the plurality of holes is substantially circular and wherein the plurality of holes comprises at least four holes, wherein the barrier directs droplets of condensed medicament toward an inner surface of the adaptor body, and wherein the insert includes a breathing gas outlet;
mixing the aerosolized medicament with a breathing gas in the mlxmg chamber to form a gas mixture; and
directing the gas mixture from the mixing chamber to a conduit fluidically coupled to a patient.

19. The method according to claim 18, wherein the step of directing the gas mixture from the mixing chamber comprises flowing the gas mixture around a baffle positioned within the adaptor body.

20. The method according to claim 18, wherein the step of directing the aerosolized medicament within the adaptor body into the mixing chamber comprises directing the droplets of condensed medicament toward a bottom surface of the adaptor body.

21. Apparatus for configuring a nebulizer with a breathing gas system, the apparatus comprising:
an adaptor having a nebulizer coupling port, an inlet port, an outlet port, and a mixing chamber between the inlet port and the outlet port, wherein the inlet port adjoins the mixing chamber; and
a barrier disposed between the nebulizer coupling port and the mixing chamber, wherein a plurality of holes are formed in the barrier, the plurality of holes opening in a direction parallel to the nebulizer coupling port and wherein each of the plurality of holes is substantially circular;
wherein the plurality of holes comprises at least four holes.

22. The apparatus of claim 21, wherein at least three of the plurality of holes are collinear.

23. The apparatus of claim 21, wherein the plurality of holes are positioned on a curved portion of the barrier.

24. The apparatus of claim 21, wherein the plurality of holes open towards the nebulizer coupling port of the adaptor.

25. The apparatus of claim 21, wherein the barrier is shaped to inhibit passage of liquid droplets from the nebulizer coupling port to the outlet port.

26. The apparatus of claim 21, wherein the barrier is shaped to conform to an inner surface of the adaptor.

27. The apparatus according to claim 21, wherein the barrier is shaped to guide liquid droplets to an inside surface of the mixing chamber.

28. The apparatus of claim 21, wherein the holes are sized to inhibit passage of liquid droplets from the nebulizer coupling port to the outlet port.

29. The apparatus according to claim 21, further comprising a baffle positioned within the adaptor.

30. The apparatus according to claim 29, wherein the baffle is positioned approximately at a cross-sectional center of the mixing chamber such that the baffle defines a channel between a peripheral edge of the baffle and an inner wall of the mixing chamber.

* * * * *

UNITED STATES PATENT AND TRADEMARK OFFICE
CERTIFICATE OF CORRECTION

PATENT NO. : 10,695,524 B2  
APPLICATION NO. : 15/636196  
DATED : June 30, 2020  
INVENTOR(S) : Felino V. Cortez, Jr. et al.

Page 1 of 1

It is certified that error appears in the above-identified patent and that said Letters Patent is hereby corrected as shown below:

In the Claims

In Claim 18, Column 8, Line 16, delete "m1xmg" and replace with --mixing--

Signed and Sealed this  
First Day of September, 2020

Andrei Iancu  
*Director of the United States Patent and Trademark Office*